United States Patent

Keil et al.

Patent Number: 5,041,553
Date of Patent: Aug. 20, 1991

[54] PROCESS FOR THE PREPARATION OF 2-SUBSTITUTED 1-(ACYLAMINOALKYL)-2-IMIDAZOLINES

[75] Inventors: Karl-Heinz Keil, Hanau-Mittelbuchen; Georg-Wolfgang Eckardt, Frankfurt am Main; Herbert Wirtz, Eppstein; Helmut Berenbold, Wiesbaden; Werner Wellbrock, Bad Soden am Taunus; Horst Fröhlich, Eppstein, all of Fed. Rep. of Germany

[73] Assignee: Cassella Aktiengesellschaft, Frankfurt am Main, Fed. Rep. of Germany

[21] Appl. No.: 584,487

[22] Filed: Sep. 17, 1990

Related U.S. Application Data

[63] Continuation of Ser. No. 453,196, Dec. 26, 1989, abandoned, which is a continuation of Ser. No. 213,780, Jun. 30, 1988, abandoned.

[30] Foreign Application Priority Data

Jul. 4, 1987 [DE] Fed. Rep. of Germany ....... 3722186

[51] Int. Cl.$^5$ ............................................. C07D 233/16
[52] U.S. Cl. ..................................... 548/352; 548/347
[58] Field of Search .......................................... 548/352

[56] References Cited

U.S. PATENT DOCUMENTS 4,233,451 11/1980 Pracht et al. ....................... 548/354

FOREIGN PATENT DOCUMENTS 1565808 4/1980 United Kingdom .

OTHER PUBLICATIONS

H. Eckert, Fett–Seifen–Anstrichmitter, 74, 527–533 (1972).

Primary Examiner—Mary C. Lee
Assistant Examiner—Jacqueline Haley
Attorney, Agent, or Firm—Connolly and Hutz

[57] ABSTRACT

In the process for the preparation of 2-substituted 1-(acylaminoalkyl)-2-imidazolines of the general formula I

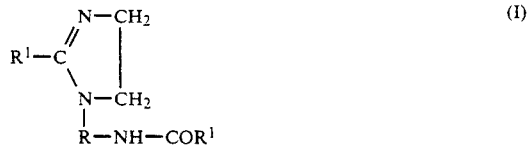

wherein R denotes an alkylene radical and $R^1$ denotes a fatty acid radical, for example, a fatty acid and a dialkylenetriamine are reacted in a molar ratio of (1.9 to 2.0):1 in such a way that the dialkylenetriamine is initially introduced hot under an inert gas atmosphere and the fatty acid is metered in hot and the amido amine formation is subsequently completed by heating to temperatures from 140° to 190° C. and the cyclization to the compound of the formula I is subsequently carried out at an under-pressure of at least 50 mbar.

9 Claims, No Drawings

PROCESS FOR THE PREPARATION OF 2-SUBSTITUTED 1-(ACYLAMINOALKYL)-2-IMIDAZOLINES

This application is a continuation of application Ser. No. 07/453,196 filed Dec. 26, 1989, now abandoned, which is a continuation of application Ser. No. 07/213,780 filed June 30, 1988, now abandoned.

The invention relates to a process for the preparation of 2-substituted 1-(acylaminoalkyl)-2-imidazolines of the general formula I

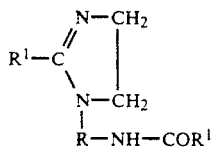 (I)

wherein R denotes an alkylene radical of the formula $-CH_2CH_2-$, $-CH_2CH_2CH_2-$ or $-CH(CH_3)CH_2CH_2-$ and $R^1$ denotes a fatty acid radical having 7 to 25 C atoms.

Compounds of the formula I where R=ethylene and trimethylene are known and are required in particular for the preparation of the corresponding quaternized imidazolinium salts (compare Kirk-Othmer, Encyclopedia of Chemical Technology, Third Edition, Volume 19, (1982), page 527), which, for their part, represent important industrial surfactants. Because of their mild and skin-compatible character, they are particularly used in the cosmetic and body care field. Compounds of the formula I having R=ethylene or trimethylene are also employed in considerable amounts in the formulation of detergents and anti-corrosion agents.

For the preparation of the compounds of the formula I having R=ethylene and trimethylene, it is known to react a fatty acid of the general formula II

 (II)

wherein $R^1$ has the meaning already mentioned, with a dialkylenetriamine of the formula III

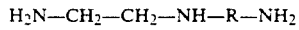 (III)

wherein R denotes ethylene ($-CH_2CH_2-$) or trimethylene ($-CH_2CH_2CH_2-$). Stoichiometrically, a molar ratio of fatty acid:dialkylenetriamine=2.0:1 is necessary for complete reaction.

For the preparation of a compound of the formula I, according to the typical example 2 of the French Patent Specification 1,582,293, a mixture of behenic acid and diethylenetriamine in a molar ratio of 2:1 is heated, for example, at 90° to 100° C. under reduced pressure in xylene for 15 hours in a nitrogen atmosphere and the water of reaction resulting from this is removed by azeotropic distillation. The xylene is subsequently removed by distillation under reduced pressure. Working in xylene and the necessity for recovery of the xylene is complicated and makes the process more expensive.

It is also already known, for the preparation of compounds of the formula I having R=ethylene and trimethylene, to react the fatty acid of the formula II and the dialkylenetriamine of the formula III having R=ethylene and trimethylene without the use of a solvent. The difficulties in the preparation of the compounds of the formula I by reaction of fatty acids of the formula II with dialkylenetriamine of the formula III consist, inter alia, in that the reaction proceeds in two steps, in which the dialkylenetriamine is first acylated by the fatty acid and this intermediate is then converted by ring closure into the compound of the formula I, and for an industrially utilizable process for the preparation of the compounds of the formula I it is required that the yield of the compounds of the formula I is high and that in the product obtained only negligible amounts of the starting products and possible acylation intermediates of the formulae IV to X

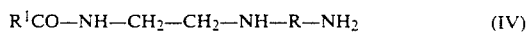 (IV)

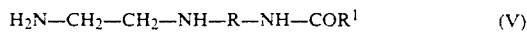 (V)

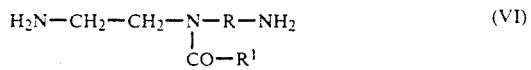 (VI)

 (VII)

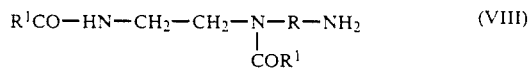 (VIII)

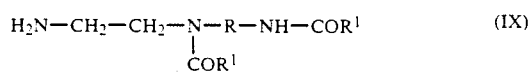 (IX)

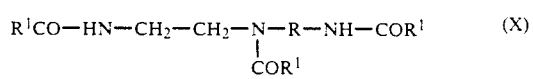 (X)

and other imidazoline compounds, for example those of the general formula XI

 (XI)

are present. For R=ethylene, the previously mentioned formulae IV and V and also VIII and IX are identical with one another.

From the investigations of Raymond G. Bistline, James W. Hampson and Warner M. Linfield in JAOCS, vol. 60, No. 4, (April 1983), pages 823 to 828, in particular page 826, it is known that in the reaction of a fatty acid of the formula II with diethylenetriamine at a temperature of 150° C., an intermediate of the above-mentioned formula VIII is predominantly formed. This intermediate can then subsequently be converted into the desired imidazoline of the formula I by heating at 150° C. under a reduced pressure of 0.2 mm/Hg. With laboratory batches, yields of 95% of the desired imidazoline of the general formula I are obtained in a cyclization period of six hours with this process. With an increase in size of the batch, considerable technical process difficulties appear because of the considerable amounts of water which are to be removed from the reaction mixture during the reaction, which difficulties finally result in that the good yields and purities obtainable with laboratory batches cannot be realized with industrial batches.

In the process of DE-A1-3,620,218, the reaction between the fatty acid of the formula II, where $R^1$ denotes an alkyl or alkenyl group having 8 to 22 C atoms, and a dialkylenetriamine of the formula III having R=ethylene and trimethylene is regulated so that first a product is formed by this which predominantly consists of an imidazoline compound of the abovementioned formula XI. This imidazoline compound of the formula XI is then subsequently converted into the desired compound of the general formula I by further reaction with the fatty acid of the formula II.

In the process of DE-A1-3,620,218 for the preparation of compounds of the formula I having R=ethylene or trimethylene 1) dialkylenetriamine having R=ethylene and trimethylene together with a higher fatty acid of the formula II, where $R^1$ denotes an alkyl or alkenyl group having 8 to 22 C atoms, or an ester thereof is introduced into a reactor in a molar ratio of fatty acid or fatty acid ester:dialkylenetriamine from 1.5:1 to 1.8:1 and 2) the reaction is carried out under reduced pressure at an internal temperature from 100° to 250° C. and 3) the higher fatty acid or an ester thereof is added to the reaction mixture so that a molar ratio of fatty acid or fatty acid ester and dialkylenetriamine of at least 2.0:1 can be achieved and 4) the reaction is continued under reduced pressure at an internal temperature from 100° to 250° C.

According to the typical Example 1 of DE-A1-3,620,218, beef tallow fatty acid and diethylenetriamine in a molar ratio of 1.8 were heated for 3 hours at 150° C. at a pressure of 400 mmHg. The temperature was then raised to 230° C. for 4 hours and the pressure simultaneously lowered to 30 mmHg. The reaction mixture was then cooled and further beef tallow fatty acid was added. The mixture was subsequently heated for 8 hours at 230° C. under a pressure of 30 mmHg. The reaction time was therefore 15 hours altogether, and the necessity to carry out all steps under reduced pressure made the process more expensive.

In addition, two substantial disadvantages in particular appear with this process on transfer to the industrial scale: 1. By working under under-pressure, uncontrollable portions of dialkylenetriamine together with the water resulting from the reaction are removed by distillation, so that the desired molar ratio cannot be accurately maintained in the industrial process. 2. Considerable amounts of trisamides of the previously mentioned formula X are formed by the joint reaction of fatty acid and dialkylenetriamine at temperatures from 140° to 170° C. These are not desired and contribute to the lowering of the activity of the compounds having the general formula I.

Surprisingly, it has now been found that it is possible to avoid the disadvantages of the previous processes for the preparation of the compounds of the formula I. The invention relates to a process for the preparation of compounds of the general formula I by reaction of a fatty acid, consisting of one or several fatty acids of the general formula II and/or one or several esters of fatty acids of the formula II and/or one or several glycerides of fatty acids of the formula II, with a dialkylenetriamine of the formula III, and is characterized in that the fatty acid component and the dialkylenetriamine of the formula III are reacted in the molar ratio (1.9 to 2.0):1 in such a way that the dialkylenetriamine is initially introduced under an inert gas atmosphere and is brought to a temperature from 100° to 190° C. and the fatty acid component is metered in as a liquid having a temperature from 100° to 190° C. and the water resulting from the reaction and/or glycerol and/or the alcohol resulting from the reaction is removed by distillation and the amidoamine formation is completed by heating to temperatures from 140° to 190° C. and the cyclization to the compound of the formula I is subsequently carried out at an underpressure of at least 50 mbar.

In the compounds of the formula I, the fatty acid radical $R^1$ having 7 to 25 C atoms in particular stands for an alkyl or alkenyl group. The alkyl and alkenyl groups can be straight-chain or branched and can also be substituted by OH. The alkenyl groups can be monounsaturated or polyunsaturated, for example diunsaturated, triunsaturated or tetraunsaturated. The fatty acid radical standing for $R^1$ is derived from fatty acids having 8 to 26 C atoms by elimination of the carboxyl group. Accordingly, the fatty acid component to be used as starting product can, for example, contain one or several fatty acids of the general formula II having 8 to 26 C atoms. Examples of fatty acids of this type are: caprylic acid, pelargonic acid, capric acid, undecanoic acid, lauric acid, myristic acid, palmitic acid, margaric acid, stearic acid, arachic acid, behenic acid, lignoceric acid, cerotic acid, tuberculostearic acid, stillingic acid, palmitoleic acid, oleic acid, ricinoleic acid, petroselinic, vaccenic acid, linoleic acid, elaeostearic acid, licanic acid, parinaric acid, arachidonic acid, erucic acid and selacholeic acid. Mixtures of these types of fatty acids can also be employed, in particular mixtures of fatty acids like those which can be obtained from solid, semi-solid or liquid fats, for example coconut oil, palm kernel oil, olive oil, castor oil, rape oil, groundnut oil, palm oil, lard or beef tallow.

The fatty acid component to be used as starting product can contain the fatty acid of formula II also in the form of an ester, in particular an alkyl ester having 1 to 4 C atoms, preferably a methyl or ethyl ester and/or also in the form of a glycerol. In the context of the present invention the esters are also taken to mean the glycerides, so that fats and oils, in particular those which contain the abovementioned fatty acids, can also be employed as esters. The fatty acid component can consist of a fatty acid, an ester or a glyceride or of a mixture of such compounds. The esters and/or glycerides (i.e. fats or oils) can thus, for example, also be employed in mixtures with one another and/or in mixtures with the fatty acids. Mixtures of fatty acids with glycerides, i.e. fatty acids with fats and/or oils, are preferred.

The diethylenetriamine of the formula XII

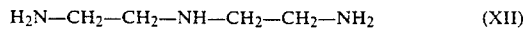

or the triamine of the formula XIII

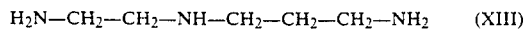

or the triamine of the formula XIV

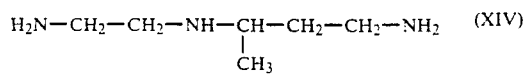

can be employed as the dialkylenetriamine of the general formula III. The compounds of the formulae XII and XIII are known. The triamine of the formula XIV can be prepared industrially by addition of ethylenediamine to crotononitrile and subsequent hydrogenation.

It is also possible to use mixtures of these three triamines. The ethylene radical (—CH$_2$CH$_2$)— is preferred for R, which means that the diethylenetriamine of the formula XII is preferably employed as the starting material of the general formula III.

When carrying out the process according to the invention, the dialkylenetriamine of the formula III is initially introduced under an inert gas atmosphere. Any gas which does not react with the starting materials and final products under the reaction conditions is suitable as the inert gas. The inert gases are suitable for example, in particular nitrogen however, which is preferred on account of its favourable price.

After the dialkylenetriamine has been initially introduced under the inert gas atmosphere, it is heated to a temperature from 100° to 190° C.

The fatty acid component, heated to a temperature from 100° to 190° C., is then metered into the heated and expediently stirred dialkylenetriamine, the amidoamine formation immediately setting in with the elimination of water, alcohol and/or glycerol. Expediently, the fatty acid component is metered in at the temperature which the initially introduced dialkylenetriamine or the reaction mixture has.

In the case where the fatty acid component consists of one or several esters of fatty acids of formula II the dialkylenetriamine is preferably heated to a temperature of 100° to 150° C., very particularly preferably to 110° to 140° C., and the fatty acid component is preferably metered in at a temperature of 100° to 150° C., very particularly preferably at 110° to 130° C.

In the case where the fatty acid component consists of one or several fatty acids of formula II the dialkylenetriamine is preferably heated to a temperature of 130° to 190° C., very particularly preferably to 150° to 170° C., and the fatty acid component is preferably metered in at a temperature of 130° to 170° C., very particularly preferably 140° to 150° C.

In the case where the fatty acid component consists of one or several glycerides of fatty acids of formula II the preferred or very particularly preferred temperature ranges indicated above for a fatty acid component consisting of fatty acids are applied for heating the dialkylenetriamine and metering in the fatty acid component.

The alcohol or the water formed in the reaction is removed continuously by distillation preferably immediately, which expediently takes place through an attached descending condenser. It is expedient to select the rate for the metering in of the hot liquid fatty acid of the general formula II in such a way that the distillate has a temperature from 90° to 100° C. in the head of the descending condenser. The rate of metering can also be automatically controlled by this head temperature of the distillate passing over. The rate of metering can also be automatically controlled, when using an ester, by the temperature of the distillate in the descending condenser. When carrying out the process on the industrial scale, the hot liquid fatty acid component can, as a rule, be metered in at a rate of 150 to 800 l/h, preferably 250 to 600 l/h.

In the case where the fatty acid component consists of or contains a glyceride, glycerol is split off in the reaction. After metering-in the fatty acid component said glycerol is removed by distillation during the formation of amidoamine and/or cyclization at an underpressure of at least 50 mbar, appropriately of at least 2 mbar.

In the case where the fatty acid component consists of one or several fatty acids of formula II and/or one or several glycerides, the initially introduced dialkylenetriamine of the formula III or the resulting reaction mixture is kept, during metering-in, preferably at a temperature from 130° to 190° C., very particularly preferably 150° to 170° C.

In the case where the fatty acid component consists of one or several esters of fatty acids of formula II, the initially introduced dialkylenetriamine of the formula III or the resulting reaction mixture is kept, during metering-in, preferably at a temperature from 100° to 150° C., very particularly preferably 110° to 140° C.

When using mixtures as fatty acid component, the mixture can be added to the initially introduced dialkylenetriamine, or the individual components of the mixture and/or the mixture can be added in any order to the initially introduced dialkylenetriamine or the reaction batch.

When using an alkyl ester of a fatty acid of the formula II, it is preferred for the acceleration of the reaction to add to the reaction mixture, relative to the ester, about 0.01 to 2.0% by weight, as a rule about 0.03 to 0.5% by weight, of a strong base, such as, for example, of an alkali metal alcoholate, such as, for example, sodium methoxide or sodium ethoxide, or potassium methoxide or potassium ethoxide, or an alkali metal hydroxide, such as, for example, sodium hydroxide or potassium hydroxide.

The amount of the fatty acid component metered into the initially introduced dialkylenetriamine of the formula III in the process according to the invention is selected in such a way that the molar ratio between fatty acid of the formula II and dialkylenetriamine of the formula III is (1.9 to 2.0):1. When calculating the molar ratio, using glycerides, it must be considered that said glycerides do not contain only one fatty acid radicals but, in the case of natural oils and fats, three fatty acid radicals. This means that the molar ratio is calculated based on 1 mol of triglyceride and 3 mols of fatty acid radicals.

After metering in the fatty acid component, the mixture is further heated to a temperature from 140° to 190° C., preferably 150° to 170° C., for completion of the amidoamine formation. The amidoamine formation is complete when, using an ester, no more alcohol escapes and, when using a fatty acid, no more water escapes. It is to be assumed that the diamidoamine of the initially mentioned formula VIII is predominantly formed in this case in the process according to the invention. Normally, the condensation phase following the completion of the metering in of the fatty acid of the formula II or its ester for completion of the amidoamine formation can be ended after 2 to 4 hours, in particular after 2½ to 3 hours.

The subsequent cyclization is carried out at an underpressure of at least 50 mbar, for example at an underpressure from 50 to 0.01 mbar, preferably at 50 to 0.1 mbar. A temperature of at least 140° C., in particular at least 170° C., preferably at least 180° C., is normally maintained in the cyclization. The cyclization can be carried out, for example, in the temperature range from 140° to 230° C., in particular 170° to 210° C. and preferably in the temperature range from 180° to 190° C. The cyclization is in most cases complete after 4 to 6 hours.

In the case where the fatty acid component contains a glyceride the glycerol split off in the reaction with the dialkylenetriamine of formula III is wholly or partially removed by distillation during the condensation phase by applying an under-pressure, in particular an under-pressure of at least 50 mbar, for example 0.01 to 50 mbar, preferably 50 to 0.1 mbar. The condensation phase gradually passes into the cyclization phase.

For the production of pale-coloured or colourless compounds of the general formula I, it is expedient to carry out the process according to the invention in the presence of 0.2 to 5% by weight of phosphorous and/or hypophosphorous acid, relative to the total weight of the starting compounds of the formula II and III. The phosphorous and/or hypophosphorous acid can in this case be added, if appropriate in the form of aqueous solutions, both to the initially introduced dialkylenetriamine of the general formula III and the fatty acid of the general formula II or its ester. It is also possible to divide the amount of phosphorous and/or hypophosphorous acid used between both starting materials of the formula II and III. The use of hypophosphorous acid is preferred.

The process according to the invention is carried out without the use of a solvent and proceeds without the use of over- or under-pressure until the concluding cyclization. No foaming or spraying or other difficulties occur in the process according to the invention through the escape of the water or alcohol formed in the reaction. The total reaction times are relatively low with an average of 7 to 9 hours and thereby make space-time yields possible which are superior to the previous processes. The yields of the compounds of the general formula I are high and are, as a rule, 90 to 98% of theory. The compounds of the formula I obtainable by the process according to the invention are so pure that they can be further used directly for the most diverse purposes without further purification or aftertreatment operations. In particular, the imidazoline compounds of the formula I preparable by the process according to the invention have a negligible content of the particularly undesirable trisamido compounds of the general formula X.

The compounds of the formula I having R=methyltrimethylene (=—CH(CH$_3$)CH$_2$CH$_2$—) are new are claimed in the context of the present invention. They possess properties which are similar to those of the known compounds of the formula I having R=ethylene (—CH$_2$CH$_2$—) and trimethylene (—CH$_2$CH$_2$CH$_2$—) and can be used for the same purposes as the compounds of the formula I having R=ethylene or trimethylene (—CH$_2$CH$_2$— or —CH$_2$CH$_2$CH$_2$—), that is to say in particular as starting materials for the preparation of corresponding quaternary nitrogen compounds having surface-active properties. They can also be employed, however, preferably in combination with other quaternary compounds, for the preparation of formulations for the treatment of textiles.

The process according to the invention is further illustrated by the following Examples 1 to 8. The following Examples 9 and 10 represent comparison examples which show that only substantially lower yields and more impure products are obtained with procedures not according to the invention. Percentages are, unless otherwise indicated, percentages by weight.

EXAMPLE 1

After evacuating and purging with nitrogen three times, 148.4 g (1.438 mol) of diethylenetriamine and 0.72 g of hypophosphorous acid (in the form of a 50% by weight aqueous solution) are initially introduced into a 3 l four-necked flask having an anchor stirrer, heatable dropping funnel, thermometer and descending condenser, covered with nitrogen and heated to an internal temperature of 155° to 160° C. with stirring. 757.2 g (2.74 mol) of tallow fatty acid are then added in 60 s from the heated dropping funnel having a temperature of 135° C.; the resultant water of condensation is in this case continuously removed by distillation via the head of the descending condenser. After the addition of the stearic acid, the mixture is condensed at 150° to 170° C. for 3 hours, and the ring closure to the imidazoline compound is subsequently carried out for 6 hours at 185° to 190° C./4 mbar.

Molar ratio of batch: tallow fatty acid:diethylenetriamine = 1.905:1.

Yield: 95.7% of theory of imidazoline compound of the formula I having R=ethylene (—CH$_2$CH$_2$—) and R$^1$ being a radical which is derived from tallow fatty acid by elimination of the carboxyl group.

| Analysis: | found | calculated |
|---|---|---|
| N (total by Kjeldahl) | 7.0% | 7.01% |
| N (basic, total) | 2.35% | 2.33% |
| N (tertiary) | 2.21% | 2.33% |
| N (primary) | 0.09% | 0% |
| N (secondary) | <<0.01% | 0% | acid number: 2.3 (corresponding to 1.1% of free tallow fatty acid)

EXAMPLE 2

750.8 g (2.74 mol) of commercial stearic acid having an acid number of 205 are employed instead of tallow fatty acid in a repetition of Example 1. The other conditions remain unchanged. Yield: 94.4% of theory of 1-(2-stearoylaminoethyl)-2-heptadecyl-2-imidazoline

| Analysis: | found | calculated |
|---|---|---|
| N (total by Kjeldahl) | 6.95% | 7.01% |
| N (basic, total) | 2.21% | 2.33% |
| N (tertiary) | 2.20% | 2.33% |
| N (primary) | 0.01% | 0% |
| N (secondary) | <<0.01% | 0% |

EXAMPLE 3

After evacuating and purging three times with nitrogen, 148.4 g (1.438 mol) of diethylenetriamine and 0.72 g of hypophosphorous acid (in the form of a 50% by weight aqueous solution) are initially introduced into a 3 l four-necked flask having an anchor stirrer, heatable dropping funnel, thermometer and descending condenser, covered with nitrogen and heated to an internal temperature of 155° to 160° C. with stirring. 804.2 g of a commercial arachic/behenic acid mixture having an acid number of 191 (2.74 mol) together with 0.723 g of hypophosphorous acid (in the form of a 50% by weight aqueous solution) are then added in 60 minutes from a heated dropping funnel having a temperature from 155° to 160° C.; the water of condensation resulting is in this case removed by continuous distillation via the head of the descending condenser. The mixture is condensed at 150° to 170° C. for 3 hours after the addition of the arachic/behenic acid mixture and subsequently heated for 4 hours at 180° to 190° C. and a vacuum of 40 mbar.

Molar ratio of batch: arachic/behenic acid:diethylenetriamine = 1.9505:1.

Yield: 97.4% of imidazoline compound of the formula I having R=ethylene (—CH$_2$CH$_2$—) and R$^1$ being a radical which is derived from arachic/behenic acid by elimination of the carboxyl group.

| Analysis | found | calculated |
|---|---|---|
| N (total by Kjeldahl) | 6.60% | 6.60% |
| N (basic, total) | 2.05% | 2.03% |
| N (tertiary) | 1.97% | 1.98% |

Acid number: 2.4 (corresponding to 1.2% of free arachic/behenic acid mixture).

EXAMPLE 4

After evacuating and purging three times with nitrogen, 142.5 g (1.38 mol) of diethylenetriamine are initially introduced into a 3 l four-necked flask, which is provided with an anchor stirrer, heatable dropping funnel, thermometer and descending condenser, covered with nitrogen and heated to an internal temperature of 155° to 160° C. with stirring, and 756.2 g (2.74 mol) of commercial stearic acid having an acid number of 203 and a temperature of 140° C. are metered into the reaction flask as a liquid and the resulting water of condensation is removed by distillation via the head of the descending condenser.

The mixture is then heated at 160° to 175° C. for 3 hours after the addition and subsequently reacted under a vacuum of 10 mbar and a temperature of 185° to 190° C. to give the imidazoline.

Molar ratio of batch: commercial stearic acid:diethylenetriamine = 1.985:1.

Yield: 92.5% of theory of imidazoline compound of the formula I having R=ethylene (—CH$_2$CH$_2$—) and R$^1$ being a radical which is derived from commercial stearic acid by elimination of the carboxyl group.

| Analysis | found | calculated |
|---|---|---|
| N (total by Kjeldahl) | 6.95% | 7.01% |
| N (basic, total) | 2.35% | 2.33% |
| N (tertiary) | 2.15% | 2.33% |

Acid number: 4.5 (corresponding to 2.2% of free commercial stearic acid).

EXAMPLE 5

After evacuating and purging three times with nitrogen, 144.85 g (1.406 mol) of diethylenetriamine and 0.71 g of hypophosphorous acid (in the form of a 50% by weight aqueous solution) are initially introduced into a 3 l four-necked flask which is provided with an anchor stirrer, heatable dropping funnel, thermometer and descending condenser, purged with nitrogen and heated to an internal temperature of 170° C. 756.2 g (2.74 mol) of tallow fatty acid are then added from a heatable dropping funnel as a liquid having a temperature of 150° C. The water resulting from the reaction is removed by distillation via the head of a column on the descending condenser. The mixture is subsequently condensed for 3 hours at 160° to 170° C., water still being removed continuously by distillation. The desired imidazoline is then obtained by heating to 185° to 190° C. in 4 hours under a vacuum of 50 mbar.

Molar ratio of batch: tallow fatty acid: diethylenetriamine = 1.95:1.

Yield: 92.5% of theory of imidazoline compound of the formula I having R=ethylene (—CH$_2$CH$_2$—) and R$^1$ being a radical which is derived from tallow fatty acid by elimination of the carboxyl group.

| Analysis | found | calculated |
|---|---|---|
| N (total by Kjeldahl) | 6.9% | 7.01% |
| N (basic, total) | 2.22% | 2.33% |
| N (tertiary) | 2.15% | 2.33% |

Acid number: 2.0 (corresponding to 0.98% free tallow fatty acid)

EXAMPLE 6

After evacuating and purging three times with nitrogen, 103 g (1 mol) of diethylenetriamine are initially introduced into a 2 l four-necked flask having an anchor stirrer, thermometer, heatable dropping funnel and descending condenser, 2.86 g of 10% strength methanolic sodium methoxyl solution are added and the mixture is heated to an internal temperature from 115° to 120° C. with the introduction of nitrogen. 568 g (1.93 mol) of methyl stearate having a temperature of 110° C. are then added from a heatable dropping funnel. The reaction temperature in the reaction flask is then raised to 150° C., by means of which a clear homogeneous reaction solution is formed and methanol is continuously removed by distillation in the descending condenser.

The mixture is subsequently condensed for 6 hours at 6 mbar and 188°–190° C.

The crude product obtained is produced in high purity and good yield.

Yield: 575 g corresponding to 96.6% of theory, content of 1-(2-stearoylaminoethyl)-2-heptadecyl-2-imidazoline: 93.13%.

| Analysis | found | calculated |
|---|---|---|
| N (total by Khjeldahl) | 7.0% | 7.01% |
| N (basic, total) | 2.29% | 2.33% |
| N (tertiary) | 2.17% | 2.33% |
| N (primary) | <0.01% | 0% |
| N (secondary) | 0.12% | 0% |

Acid number: 4.7 (corresponding to 2.38% of free commercial stearic acid).

EXAMPLE 7

After evacuating and purging three times with nitrogen, 0.222 kg (2.15 mol) of diethylenetriamine are initially introduced into a 5 l VA pressure vessel, which is provided with a thermometer, anchor stirrer and bottom valve, and heated to an internal temperature of 150° C.

1152.9 g (4.19 mol) of liquid commercial stearic acid (molecular weight 275, acid number 204) having a temperature of 150° C. is then added in 90 s from a heatable dropping funnel and the resulting water of condensation is immediately removed by distillation. No spontaneous formation of water and thus no increase in pressure is observed. The mixture is subsequently condensed for 3 hours at 160° to 170° C., water continuously being removed by distillation in the descending condenser. The reaction is completed by heating to 180° to 190° C. in 6 hours in a vacuum of 0.1 mbar.

Yield: 1250 g=99.1% of theory, Content of 1-(2-stearoylaminoethyl)-2-heptadecyl-2-imidazoline 95.7%

Molar ratio of batch: commercial stearic acid: diethylenetriamine = 1.9452:1

| Analysis | found | calculated |
|---|---|---|
| N (total by Kjeldahl) | 6.95% | 7.01% |
| N (basic, total) | 2.45% | 2.33% |
| N (tertiary) | 2.17% | 2.33% |
| N (primary) | 0.28% | 0% |
| N (secondary) | <<0.01% | 0% |

Acid number: 1.2 (corresponding to 0.61% of free commercial stearic acid)

EXAMPLE 8

After evacuating and purging three times with nitrogen, 131 g (1 mol) of 1-(3-amino-1-methylpropyl)ethylenediamine are initially introduced into a 3 l four-necked flask having an anchor stirrer, thermometer, heatable dropping funnel and descending condenser, 1.31 g of hypophosphorous acid are added and the mixture is heated to an internal temperature of 160° C. 533.5 g (1.94 mol) of commercial stearic acid (acid number: 204) having a temperature of 150° C. are then metered in in 2 minutes from a heatable dropping funnel and the resulting water of reaction is continuously removed by distillation via the head of the descending condenser. The mixture is then condensed for 5 hours at 170° C. The cyclization to the imidazoline is concluded in 8 hours by heating to 180° to 190° C. at 0.1 mbar.

Molar ratio of batch: commercial stearic acid: 1-(3-amino-1-methylpropyl)ethylenediamine = 1.94:1.

Yield: 604 g corresponding to 98.6% of theory, content of imidazoline compound of the formula I having R=methyltrimethylene (—CH(CH$_3$)CH$_2$CH$_2$—) and R$^1$=heptadecyl:92.7%

| Analysis | found | calculated |
|---|---|---|
| N (total by Kjeldahl) | 6.08% | 6.16% |
| N (basic, total) | 1.96% | 2.05% |
| N (tertiary) | 1.90% | 2.05% |
| N (primary) | 0.15% | 0% |
| N (secondary) | <<0.01% | 0% |

Acid number: 1.8 (corresponding to 0.88% of free commercial stearic acid)

Other fatty acids of the formula II can also be employed instead of stearic acid with equally good results.

EXAMPLE 9 (COMPARISON EXAMPLE)

After evacuating and purging three times with nitrogen, 0.222 kg (2.15 mol) of diethylenetriamine are initially introduced into a 5 l VA pressure vessel which is provided with a thermometer, anchor stirrer and bottom valve, and 1.215 kg (4.40 mol) of stearic acid are added as a liquid having a temperature from 70° to 75° C. Both reactants are subsequently heated. In this way a paste is formed which can only be stirred with difficulty. This becomes clear at 135° C., and at 145° to 150° C. the reaction sets in spontaneously, so that the reaction can only be conducted under an over-pressure up to 2 bar. After depressurizing, the mixture is condensed for 6 hours at 170° to 190° C. and 10 mbar.

The starting molar ratio is: stearic acid: diethylenetriamine = 2.05:1.

Yield: 84.9% of theory of 1-(2-stearoylaminoethyl)-2-heptadecyl-2-imidazoline

| Analysis | found | calculated |
|---|---|---|
| N (total by Kjeldahl) | 6.85% | 7.01% |
| N (basic, total) | 2.25% | 2.33% |
| N (tertiary) | 1.97% | 2.33% |
| N (primary) | 0.27% | 0% |
| N (secondary) | 0.1% | 0% |

Acid number: 5 (corresponding to 2.4% of free stearic acid)

EXAMPLE 10 (COMPARISON EXAMPLE)

After evacuating and purging three times with nitrogen, 1.5 kg (5.43 mol) of stearic acid are initially introduced into a 5 l VA pressure vessel, which is provided with a thermometer, anchor stirrer and bottom valve, and melted with 1.66 g of hypophosphorous acid and heated to an internal temperature from 120° to 130° C. 295 g (2.86 mol) of diethylenetriamine having a temperature of 130° C. are then added under pressure from a second 1 l VA pressure vessel. After 3 minutes, the reaction sets in spontaneously with foaming, and a pressure of 1.5 bar is measured in the reaction vessel.

After depressurizing, water is removed by distillation at a temperature from 150° to 170° C. in the descending condenser and the reaction is completed under 10 mbar in 4 hours at 180° to 190° C. Starting molar ratio: stearic acid: diethylenetriamine = 1.89:1 Yield: 78.0% of theory of 1-(2-stearoylaminoethyl)-2-heptadecyl-2-imidazoline

| Analysis | found | calculated |
|---|---|---|
| N (total by Kjeldahl) | 6.9% | 7.01% |
| N (basic, total) | 2.06% | 2.33% |
| N (tertiary) | 1.81% | 2.33% |
| N (primary) | 0.25% | 0% |
| N (secondary) | 0.1% | 0% |

Acid number: 9.5 (corresponding to 3.44% of free stearic acid)

EXAMPLE 11

475 g (4.61 mol) of diethylenetriamine are initially introduced into a 5 l four-necked stirring flask, which is provided with an anchor stirrer, thermometer, heatable dropping funnel and reflux condenser, and the flask is evacuated twice. It is then purged with nitro-gen and heated to an internal temperature from 150°–155° C. with stirring. 2841 g (9.00 mol) of hardened beef tallow having a hydrolysis number of 185 are now added from a heatable dropping funnel at a temperature of 150°–155° C. during the course of 5 minutes and subsequently stirred for 2 hours at 160°–170° C. The reflux condenser is then exchanged for a descending condenser and a mixture of glycerol, water and a little diethylenetriamine is removed by distillation at 130°–160° C. at a bath temperature of 188°–200° C. (internal temperature maximum 190° C.) at 2–3 mbar.

Water and the residual glycerol are then constantly removed for 6 hours by distillation at 188°–190° C. internal temperature in the descending condenser. The product obtained possesses a high purity and practically no by-products.

Molar ratio of batch: Beef tallow: diethylenetriamine = 1.952:1

Yield: 94.4% of theory of imidazoline compound of the formula I

| Analysis | found | calculated |
|---|---|---|
| N (tertiary) | 2.20% | 2.33% |
| N (primary + secondary) | <0.1% | 0 |

Acid number: 2.9 (corresponding to 1.1% of free beef tallow fatty acid).

EXAMPLE 12

486.6 g (4.72 mol) of diethylenetriamine are initially introduced into a 5 l four-necked stirring flask which is provided with an anchor stirrer, thermometer, heatable dropping funnel and reflux condenser, and the flask is evacuated twice. It is then purged with nitrogen and heated to an internal temperature of 150°–155° C. with stirring. 2841 g (9.00 mol) of hardened beef tallow having a hydrolysis number of 185 are now added in 5 minutes at a temperature of 150°–155° C. and kept at 170°–175° C. for 2 hours. The reflux condenser is subsequently replaced by a descending condenser and a mixture of gly-cerol, water and small amounts of diethylenetriamine is removed by distillation at a bath temperature of 180° to 200° C. (internal temperature maximum 190° C.).

The mixture is subsequently removed by distillation at 2–3 mbar for a further 6 hours at 188°–190° C. internal temperature in the descending condenser.

The product obtained in the preparation procedure described above is distinguished by high purity and low amounts of by-products.

Molar ratio of batch: Beef tallow: diethylenetriamine = 1.906:1.

Analysis:
$N_{tert}$: found: 2.21%; calc.: 2.33%.
Imidazoline content: 95%.
Triamide content <4%.
Glycerol content: <0.5%.
$N_{prim} + N_{sec}$: <0.1%.

EXAMPLE 13

362.3 g (3.51 mol) of diethylenetriamine and 1.76 g of hypophosphorous acid are initially introduced into a 5 l four-necked stirring flask which is provided with an anchor stirrer, thermometer, heatable dropping funnel and reflux condenser, evacuated twice, rendered inert using nitrogen and brought to an internal temperature of 140°–141° C.

1295.6 g (4.69 mol) of hardened tallow fatty acid and 635 g (0.67 mol) of hardened beef tallow having a temperature of 140°–142° C. are now added in 60 minutes from a heated dropping funnel at a temperature of 140°–145° C., by means of which a mixture of water and small amounts of diethylenetriamine is continuously removed by distillation in the descending condenser. Finally, a mixture of water and glycerol is removed by distillation at an internal temperature of 188°–190° C. for 6 hours more at 2–3 mbar.

The crude product obtained is distinguished by high purity and low concentrations of possible by-products.

$N_{tert}$: found: 2.16%; calc.: 2.33%.
Imidazoline content from $N_{tert}$ 93.1%.
Tristearoyldiethylenetriamine: <4%.
$N_{prim} + N_{sec}$: <0.1%.
Glycerol: <0.5%.

Acid number: 5.1 corresponding to 2.5% free tallow fatty acid Reaction ratio: Tallow fatty acid 1.908 mol: 1.0 mol diethylenetriamine, the tallow fatty acid being composed of 70 mol% of free tallow fatty acid and 30 mol% of tallow fat triglyceride.

EXAMPLE 14

316.7 g (3.07 mol) of diethylenetriamine are initially introduced into a 5 l four-necked stirring flask which is provided with an anchor stirrer, thermometer, heatable dropping funnel and reflux condenser, and the flask is evacuated twice, rendered inert with nitrogen and heated to an internal temperature of 150°–155° C. 1492.3 g (5.4 mol) of stearic acid having an acid number of 203 and a temperature of 150°–155° C. are now added from the heatable dropping funnel during the course of 120 minutes and the water formed during the reaction is continuously removed by distillation. Additionally, a further 215 g (0.22 mol) of hardened beef tallow also having a temperature of 150°–155° C. are subsequently added. In this way, a mixture of water, glycerol and small amounts of diethylenetriamine is removed by distillation.

The reaction is carried on for a further 6 hours at 2–3 mbar/188°–189° C., a very pure crude product without by-products resulting.

Found: $N_{tert}$ 2.12%; calc.: $N_{tert}$ 2.33%.
Imidazoline content from $N_{tert}$ 91.0%.
Tristearoyldiethylenetriamine ≦4%.
Glycerol content: <0.5%.
$N_{prim} + N_{sec}$: <0.2%.

Acid number: 4.2 corresponding to 2.1% of tallow fatty acid.

EXAMPLE 15

316.7 g (3.07 mol) of diethylenetriamine are initially introduced into a 3 l stirring flask which is provided with an anchor stirrer, gas inlet tube, heatable dropping funnel and descending condenser. The flask is evacuated twice, purged with nitrogen and, after adding 3.15 g of hypophosphorous acid (50% strength aqueous solution), heated to an internal temperature of 155°–160° C. 18.9 g (0.02 mol) of tallow fatty acid triglyceride having a hydrolysis number of 185 and a temperature of 150° C. are now added from the heatable dropping funnel during the course of 2 minutes and a further 1136.4 g (5.94 mol) of hardened tallow fatty acid having a temperature of 155°–160° C. are subsequently added with stirring at 153° to 170° C. for 1 hour. While metering-in the tallow fatty acid water is continuously removed by distillation. Subsequently, the batch is heated to 180° C. in the course of 1 hour and then the cyclization is continued at 189° to 190° C. in 9 hours and at 2 mbar to give the desired imidazoline.

The imidazoline product obtained features a high degree of purity and a low concentration of possible by-products.

Yield: 1960 g corresponding to 99% of theory.
Found: $N_{tert}$ 2.20%; calc.: $N_{tert}$ 2.33%.
Imidazoline content from $N_{tert}$ calc.: 94.4%.
Tristearoyldiethylenetriamine <4%.
Glycerol <0.2%.

Acid number: 3.9 corresponding to 1.9% of hardened free tallow fatty acid.

Molar ratio od reaction: Hardened tallow fatty acid: diethylenetriamine = 1.95 mol: 1.0 mol, the tallow fatty acid component being composed of 99% of free hardened tallow fatty acid and 1 mol% of free hardened tallow fatty acid in the form of tallow fatty triglyceride.

EXAMPLE 16

316.7 g (3.07 mol) of diethylenetriamine are initially introduced into a 3 l stirring flask which is provided with an anchor stirrer, gas inlet tube, heatable dropping funnel and descending condenser. The flask is evacuated twice, purged with nitrogen and, after adding 3.15 g of hypophosphorous acid (50% strength aqueous solution), heated to an internal temperature of 155°-160° C. 1575.2 g (5.7 mol) of hardened tallow fatty acid having a hydrolysis number of 203 and a temperature of 150° C. are now added from the heatable dropping funnel in the course of 70 minutes. Subsequently a further 94.7 g (0.1 mol) of tallow fatty triglyceride (hydrolysis number: 185) having a temperature of 150° C. are added in the course of 10 minutes, water which is admixed with small amounts of diethylenetriamine being distilled off at the descending condenser throughout the entire metering-in operation.

The batch is heated to 180° C. in 1 hour then condensed at 189°-190° C. in the course of 9 hours, the residual water and small amounts of glycerol distilling off.

Yield: 1960 g corresponding to 99% of theory.

The imidazoline product obtained features a high degree of purity and a low concentration of possible by-products.

Found: $N_{tert}$ 2.12%; calc.: $N_{tert}$ 2.33%.
Imidazoline content from $N_{tert}$ calc.: 90.9%.
$N_{prim} + N_{sec}$: <0.1%.
Tristearoyldiethylenetriamine <4%.
Glycerol <0.2%.
Acid number: 4.0 corresponding to 2% of hardened free tallow fatty acid.

Molar ratio od reaction: Hardened tallow fatty acid: diethylenetriamine=1.954 mol: 1.0 mol, the tallow fatty acid component being composed of 95 mol% of free hardened tallow fatty acid and 5 mol% of free hardened tallow fatty acid in the form of tallow fatty triglyceride.

We claim:

1. Process for the preparation of 2-substituted 1-(acylaminoalkyl)2-imidazolines of the formula I

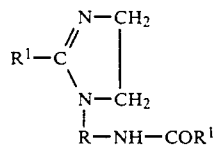

wherein
R denotes an alkylene radical of the formula
—CH$_2$CH$_2$—, —CH$_2$CH$_2$CH$_2$— or —CH(CH$_3$)CH$_2$CH$_2$— and
R$^1$ denotes a fatty acid radical having 7 to 25 C atoms,
by reaction of a fatty acid component consisting of one or several fatty acids of the formula II

R$^1$COOH (II)

or one or several esters of fatty acids of formula II or one or several glycerides of fatty acids of formula II, with a dialkylenetriamine of the formula III

H$_2$N—CH$_2$—CH$_2$—NH—R—NH$_2$ (III)

where R and R$^1$ possess the meanings mentioned, characterized in that the fatty acid of the formula II or its ester and the dialkylenetriamine of the formula III are reacted in a molar ratio of (1.9 to 2.0):1 in such a way that the dialkylenetriamine is initially introduced under an inert gas atmosphere and is brought to a temperature from 100° to 190° C. and the fatty acid component is metered in as a liquid having a temperature from 100° to 190° C. and the water resulting from the reaction or the alcohol resulting from the reaction or glycerol is removed by distillation and the amidoamine formation is completed by heating to temperatures from 140° to 190° C. and the cyclization to the compound of the formula I is subsequently carried out at a reduced pressure of at least 50 mbar.

2. Process according to claim 1, characterized in that diethylenetriamine of the formula XII

H$_2$N—CH$_2$—CH$_2$—NH—CH$_2$—CH$_2$—NH$_2$ (XII)

is employed as the compound of the formula III.

3. Process according to claim 1, characterized in that the metering-in of a fatty acid component consisting of one or several esters of fatty acids of formula II the dialkylenetriamine of formula III is heated to a temperature of 100° to 150° C. and the fatty acid component is metered in at a temperature of 100° to 150° C.

4. Process according to claim 1 characterized in that in the metering-in of a fatty acid component consisting of one or several fatty acids of formula II the dialkylenetriamine of formula III is heated to a temperature of 130° to 190° C. and the fatty acid component is metered in at a temperature of 130° to 170° C.

5. Process according to claim 1, characterized in that in the metering-in of a fatty acid component consisting of one or several glycerides of fatty acids of formula II the dialkylenetriamine of formula III is heated to a temperature of 130° to 190° C. and the fatty acid component is metered in at a temperature of 130° to 170° C.

6. Process according to claim 1, characterized in that the water resulting from the metering-in of the fatty acid component in the reaction mixture or the resulting alcohol is immediately removed by distillation.

7. Process according to claim 1, characterized in that the cyclization is carried out at a temperature of 140° to 230° C., and at a pressure of 50 to 0.01 mbar.

8. Process according to claim 1, characterized in that it is carried out in the presence of 0.2 to 5% by weight of phosphorous or hypophosphorous acid, relative to the total weight of the starting compounds of the formulae II and III.

9. Process according to claim 1, characterized in that the metering-in of an alkyl ester of a fatty acid of the formula II, 0.01 to 2% by weight of a stong base, relative to ester, is added.

* * * * *